US011828747B2

United States Patent
Khosroshahi et al.

(10) Patent No.: US 11,828,747 B2
(45) Date of Patent: Nov. 28, 2023

(54) MULTIMODAL NANOBIOSENSOR FOR DETECTING CANCER BIOMARKERS IN BLOOD SERUM

(71) Applicant: M.I.S. Electronics Inc., Richmond Hill (CA)

(72) Inventors: Mohammad E Khosroshahi, Richmond Hill (CA); Yesha Patel, Richmond Hill (CA)

(73) Assignee: M.I.S. ELECTRONICS INC., Richmond Hill (CA)

( * ) Notice: Subject to any disclaimer, the term of this patent is extended or adjusted under 35 U.S.C. 154(b) by 0 days.

(21) Appl. No.: 17/536,017

(22) Filed: Nov. 27, 2021

(65) Prior Publication Data

US 2023/0168239 A1    Jun. 1, 2023

(51) Int. Cl.
*G01N 33/49*    (2006.01)
*G01N 21/65*    (2006.01)
(Continued)

(52) U.S. Cl.
CPC ............ *G01N 33/49* (2013.01); *G01N 21/31* (2013.01); *G01N 21/6486* (2013.01);
(Continued)

(58) Field of Classification Search
None
See application file for complete search history.

(56) References Cited

U.S. PATENT DOCUMENTS

| 6,322,223 B1* | 11/2001 | Smith ................. G01J 3/0202 |
| | | 248/476 |
| 2011/0058164 A1* | 3/2011 | Zhang ................. B82Y 20/00 |
| | | 356/301 |

(Continued)

FOREIGN PATENT DOCUMENTS

| CN | 212321444 U | * | 1/2021 | |
| CN | 113203723 A | * | 8/2021 | |
| EP | 3121587 A1 | * | 1/2017 | ........... B01L 3/5027 |

OTHER PUBLICATIONS

Lee, J.- Y. et al., "Ultraviolet plasmonic enhancement of the native fluorescence of tryptophan on aluminum nano-hole arrays." Journal of Physics D: Applied Physics 54.13 (2021): 135107 (Year: 2021).*

(Continued)

*Primary Examiner* — Tarifur R Chowdhury
*Assistant Examiner* — Roberto Fabian, Jr.
(74) *Attorney, Agent, or Firm* — Jenna L. Wilson; Wilson Lue LLP (57) ABSTRACT

An optical multimodal detection system for targeted detection of cancer biomarkers in blood serum. The system comprises of a nano-biosensor, a chamber for receiving the nano-biosensor, a localized surface plasmon resonance (LSPR) based detector, a plasmon enhanced fluorescence (PEF) based detector and a surface-enhanced Raman scattering (SERS) based detector. The nano-biosensor comprises of a glass substrate provided with an active site for receiving a sample of blood serum, and is dimensioned to define a flow channel for introducing the sample of blood serum into the (Continued)

nano-biosensor. The nano-biosensor is provided with a layer of amino-silane compound coating over the glass substrate and a plurality of gold nano-urchins (GNU) bound to the layer of silicone compound. The plurality of gold-nano-urchins are functionalized with a hydrazide linker molecule for allowing uniform-oriented conjugation of a $F_c$ region of antibodies to a surface of gold nano-urchins thereby allowing Fab regions of antibodies for binding with cancer biomarkers.

8 Claims, 7 Drawing Sheets

(51) Int. Cl.
  *G01N 21/31* (2006.01)
  *G01N 21/64* (2006.01)
(52) U.S. Cl.
  CPC ..... *G01N 21/658* (2013.01); *G01N 2201/061* (2013.01); *G01N 2201/08* (2013.01)

(56) References Cited

U.S. PATENT DOCUMENTS

| | | | |
|---|---|---|---|
| 2015/0037818 A1* | 2/2015 | Huang | C23C 18/1889 427/127 |
| 2015/0247846 A1* | 9/2015 | Gerion | G01N 21/554 702/19 |
| 2018/0209909 A1* | 7/2018 | Jian | G01J 3/0208 |
| 2018/0348118 A1* | 12/2018 | Khosroshahi | G01N 29/2418 |

OTHER PUBLICATIONS

You, P.-Y. et al. "Colorimetric and fluorescent dual-mode immunoassay based on plasmon-enhanced fluorescence of polymer dots for detection of PSA in whole blood." ACS applied materials & interfaces 11.10 (Year: 2019).*

Li, Ming, et al. "Three-dimensional hierarchical plasmonic nano-architecture enhanced surface-enhanced Raman scattering immunosensor for cancer biomarker detection in blood plasma." ACS nano 7.6 (2013): 4967-4976 (Year: 2013).*

* cited by examiner

MULTIMODAL NANOBIOSENSOR FOR DETECTING CANCER BIOMARKERS IN BLOOD SERUM

BACKGROUND

Field of Invention

The disclosed subject matter relates to the field of non-invasive cancer biomarker detection. More particularly, but not exclusively, the subject matter relates to a multimodal detection system for detecting cancer biomarkers in blood serum.

Background of Invention

Diagnosis of cancer at the right time is very much needed as early diagnosis helps one take necessary precaution or treatment for early recovery. Early diagnosis would also mean that the cancer could be treated at a much early stage thereby providing a chance of restricting the growth of cancer and therefore reducing any further threats.

There are multiple forms of testing available for cancer diagnosis and monitoring its progression. With many of these tests requiring expensive equipment, long wait times, and invasive procedures, there is an urgency for cancer detection methods that can yield quick results without the use of medical imaging or autopsies. Cancer biomarkers present in blood serum can be used to develop new diagnostic technologies that only require a simple blood sample from the patient. Cancer biomarkers can be molecules that are either secreted by tumour cells or produced as a specific response to the presence of cancer in the body. Detection of cancer biomarkers in serum can not only help diagnose cancer but also monitor the effectiveness of treatment programs.

Having said that, limitation of cancer biomarker detection is the low abundance of biomarkers in blood serum. This is where nano-biosensors have proven to be advantageous due to their ability to detect low abundance analytes. Research has been conducted on the use of nano-biosensors for targeted detection of analytes by means of antibody-analyte specificity. Most nano-biosensors employ the use of gold thin films or spherical gold nanoparticles (GNP) conjugated to antibodies (Ab) that can vary based on analyte of interest.

Antibodies are Y-shaped proteins that are produced to specifically target certain analyte molecules (also referred to as antigens). Cancer biomarkers can act as antigens and each type of biomarker has a specific commercially available antibodies that can be conjugated to a gold surface through different covalent conjugation methods. Each type of conjugation chemistry will result in different orientations of the antibodies on the gold surface, and this orientation plays an important role in the sensitivity of the nano-biosensor.

Conventional antibody-gold conjugation methods involve carbodiimide (EDC) and N-hydroxy sulfo-succinimide (sulfo-NHS) chemistry or similar methods that result in the random orientation of antibodies across the gold surface. These reaction chemistries are not specific to the Fc region (fragment crystallizable region) (anchor) of antibodies and consequently there will be orientations where the Fab region (fragment antigen-binding region) (biomarker-binding region) is bound to the gold surface, making the Fab region unavailable for biomarker binding.

In view of the foregoing, there is a need for an improved cancer detection system that is accurate to detect cancer biomarkers at a very early stage and efficient to provide the results in a shorter time span.

SUMMARY

An embodiment provides a multimodal detection system for detecting cancer biomarkers in blood serum. The system comprises of a nano-biosensor, a chamber for receiving the nano-biosensor, a localized surface plasmon resonance (LSPR) based detector, a plasmon enhanced fluorescence (PEF) based detector and a surface-enhanced Raman scattering (SERS) based detector. The nano-biosensor comprises of a glass substrate provided with an active site for receiving a sample of blood serum. The glass substrate is dimensioned to define a flow channel for introducing the sample of blood serum into the nano-biosensor and onto the active site. The nano-biosensor is provided with a layer of amino-silane compound coating over the glass substrate and a plurality of gold nano-urchins bound to the layer of silicone compound. The plurality of gold-nano-urchins are functionalized with a hydrazide linker molecule for allowing uniform-oriented conjugation of a $F_c$ region of antibodies to a surface of gold nano-urchins thereby allowing $F_{ab}$ regions of antibodies for binding with cancer biomarkers.

The presence of cancer biomarkers in the blood serum is detected based on the analysis of blood serum by the localized surface plasmon resonance (LSPR) based detector, the plasmon enhanced fluorescence (PEF) based detector and the surface-enhanced Raman scattering (SERS) based detector.

BRIEF DESCRIPTION OF DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form a part of the detailed description. The drawings show illustrations in accordance with example embodiments. These example embodiments, which may be herein also referred to as "examples" are described in enough detail to enable those skilled in the art to practice the present subject matter.

However, it may be apparent to one with ordinary skill in the art, that the present invention may be practiced without these specific details. In other instances, well-known methods, procedures and components have not been described in detail so as not to unnecessarily obscure aspects of the embodiments. The embodiments can be combined, other embodiments can be utilized, or structural, logical, and design changes can be made without departing from the scope of the claims. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Figure 1:
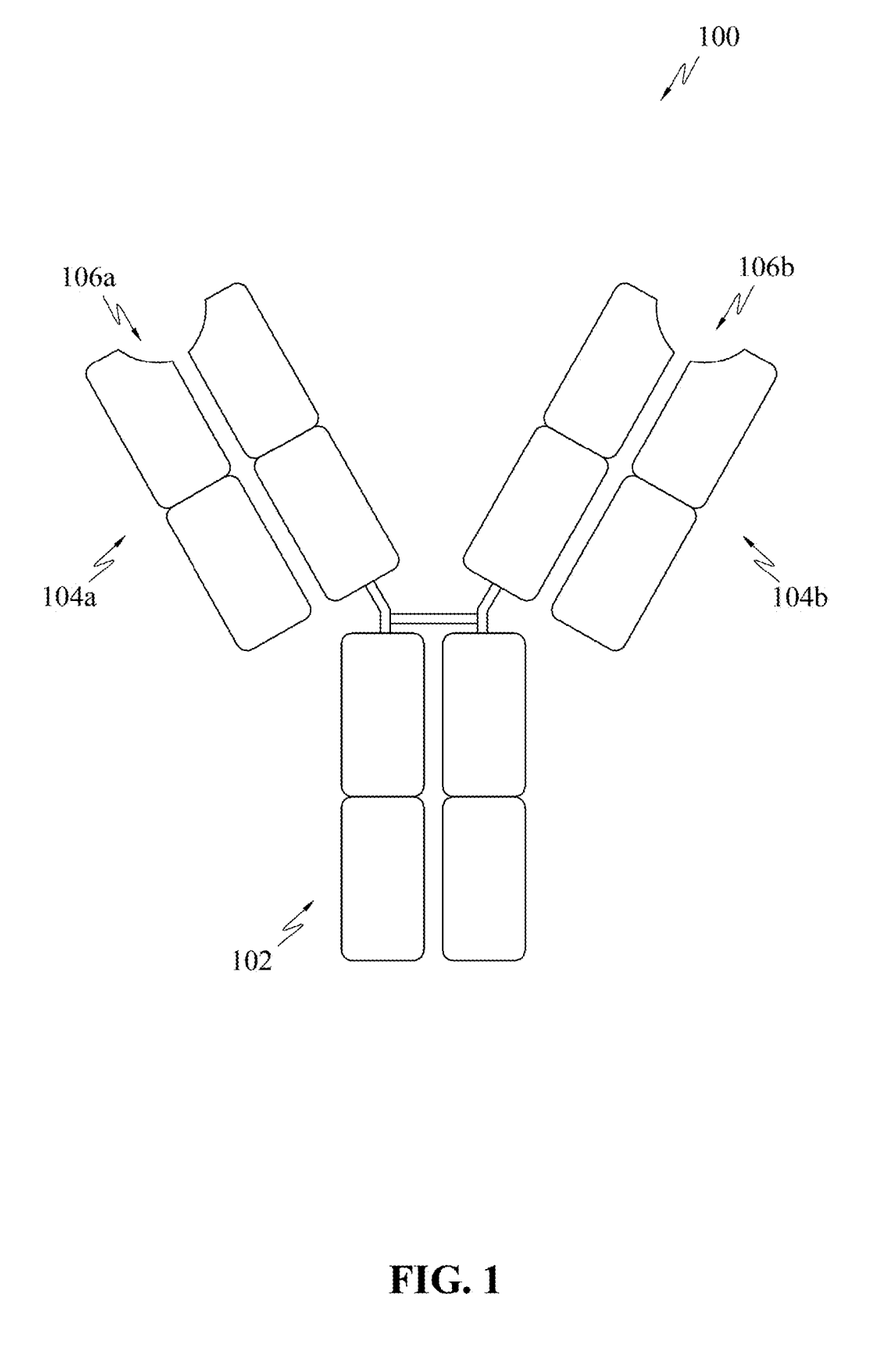
FIG. 1 illustrates anatomy of an antibody 100 comprising of $F_c$ 102 and $F_{ab}$ 104a, 104b regions.

Referring to FIG. 1, a schematic representation of an antibody 100 is disclosed. Antibodies 100 are protective proteins produced in a body by plasma cells (White Blood Cells) when the immune system detects the presence of a foreign substance called an antigen. Antibodies 100 are Y-shaped proteins that engage with the antigens to remove the antigens from the body. Antibodies are composed of two heavy protein chains paired with two light protein chains. These chains together create distinct regions, one $F_c$ region 102 and two $F_{ab}$ regions 104a, 104b, wherein $F_c$ region is fragment crystallizable region forming a tail region of the antibody and the $F_{ab}$ region is fragment antigen-binding region that comprises of antigen binding sites 106a, 106b configured to bind with the antigens.

Figure 2:
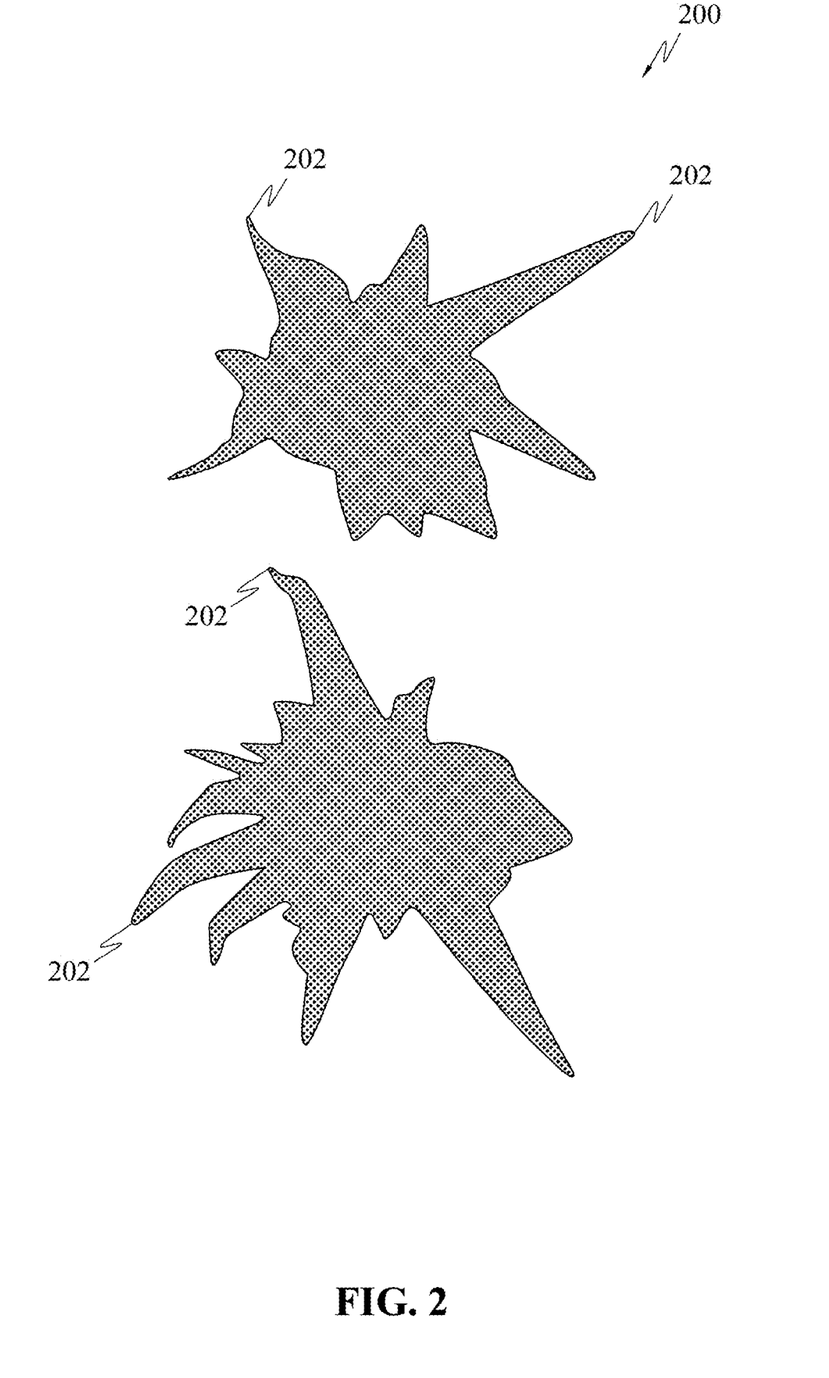
FIG. 2 illustrates gold nano-urchins 200 with spikes 202.

Referring to FIG. 2, gold nano-urchins 200 are disclosed. Gold nano-urchins 200 are also known as gold nanoflowers are multibranched nanoparticles. Gold nanoparticles are used in resonance scattering dark-field microscopy for the detection of microbial cells, detection of cancer biomarkers 316 and bio-imaging of tumour cells, among others. Gold nano-urchins 200 have spikes 202 on their surface that cause red shift in surface plasmon peak and a larger enhancement of electromagnetic field at tips of the spikes 202. With the said advantage, the employment of gold nano-urchins 200 provides a more accurate result as compared to the employment of conventional gold nanoparticles. Gold nano-urchins 200 are used in the present system instead of traditional thin gold films or gold nanoparticles for generating an enhanced electromagnetic field.

Referring to FIGS. 3A-3E, a schematic diagram of a multimodal detection system 300 for detecting cancer biomarkers 316 in blood serum and a nano-biosensor 302 is disclosed, in accordance with an embodiment. The system 300 comprises of nano-biosensor 302 (refer FIG. 3B). The nano-biosensor 302 comprises of a glass substrate 304, wherein the glass substrate 304 may be dimensioned to define a flow channel 306, wherein the flow channel 306 may have, but not limited to, a U-shaped cross section (refer FIG. 3B). The flow channel 306 may be defined by the glass substrate 304 with one horizontal surface 308 and two vertical surfaces 310a, 310b on either longitudinal side of the horizontal surface thereby forming the U-shape. The flow channel 306 of the nano-biosensor 302 may be configured for introducing sample of blood into the nano-biosensor 302. The horizontal surface 308 of the glass substrate 304 may be provided with an active site 312, wherein the active site 312 may be configured to receive the sample of blood introduced via the flow channel 306 of the nano-biosensor 302. A layer 314 of amino-silane compound may be coated over the active site 312 of the nano-biosensor 302. The amino-silane compound may be, but not limited to, (3-Aminopropyl) triethoxysilane (APTES).

Figure 3A:
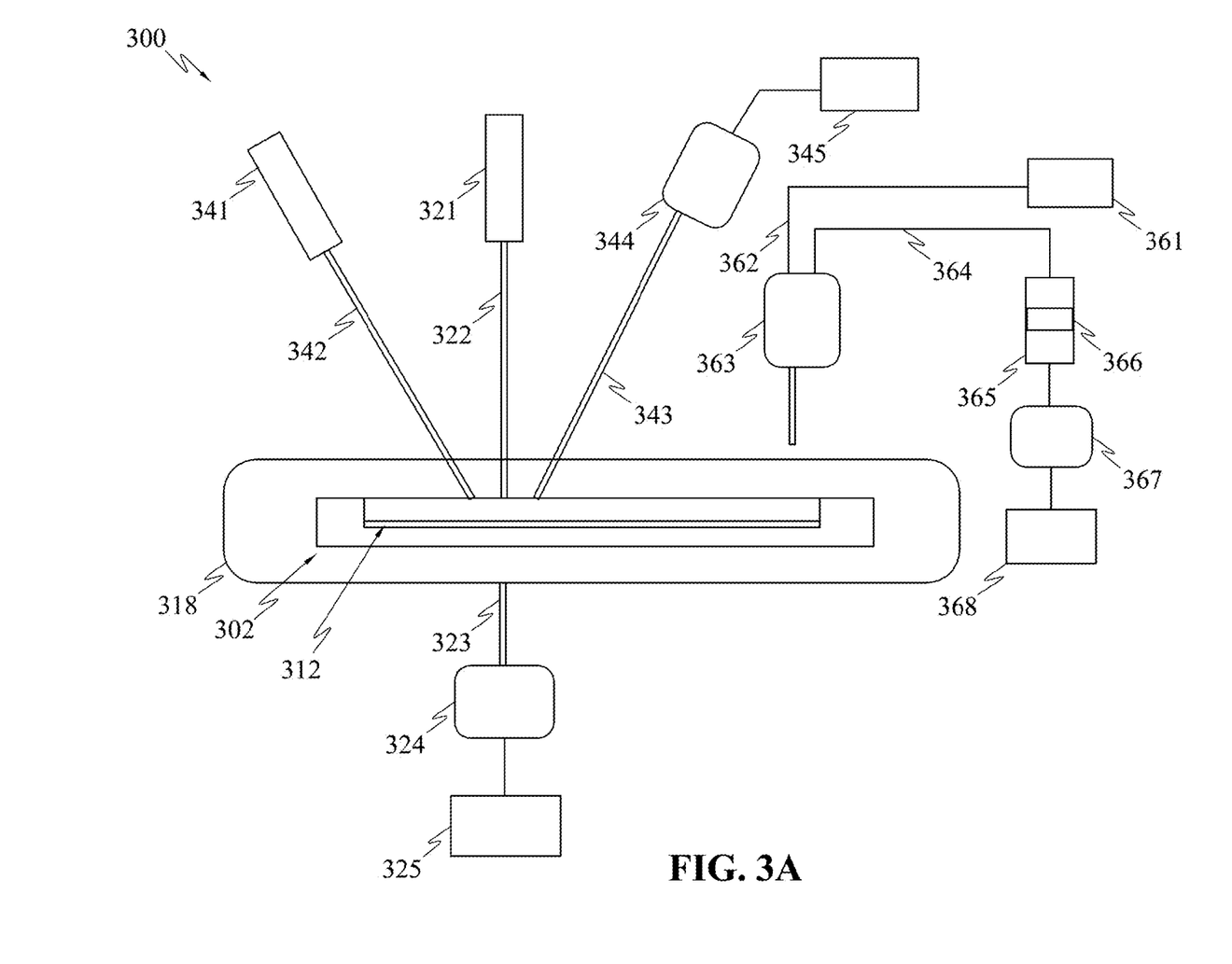
FIG. 3A is a schematic representation of multimodal detection system 300, in accordance with an embodiment.
Figure 3B:
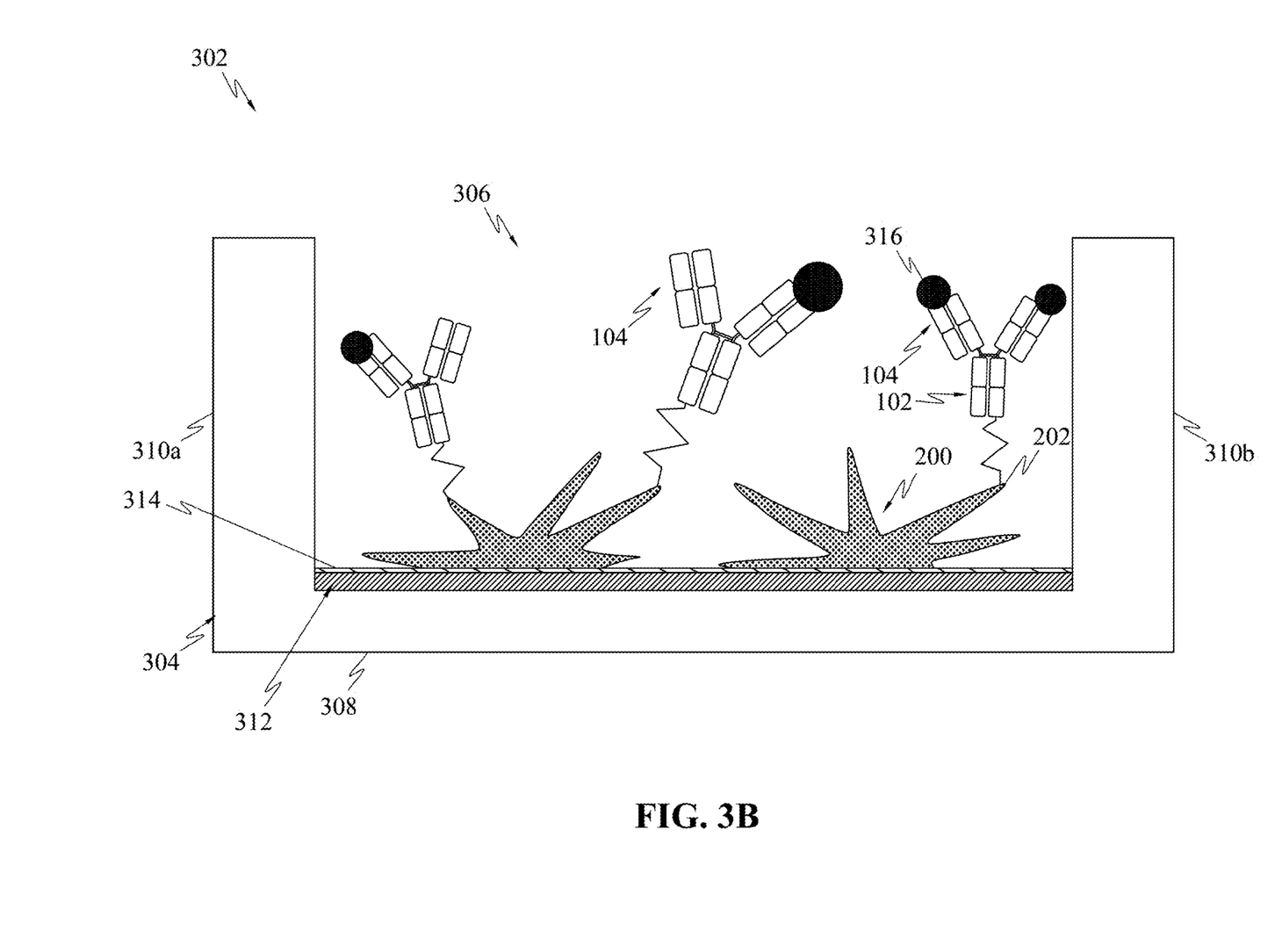
FIG. 3B illustrates a schematic view of a nano-biosensor 302 configured for receiving blood serum sample, in accordance with an embodiment.

In an embodiment, the nano-biosensor 302 may be provided with a plurality of gold nano-urchins 200. The gold nano-urchins 200 may be introduced onto the active site 312 of the nano-biosensor 302. The APTES layer 314 coating provided on the active site 312 of the nano-biosensor 302 may facilitate binding of the gold nano-urchins 200 to the amino-silane compound i.e., APTES layer 314. The gold nano-urchins 200 introduced in the flow channel 306 of the nano-biosensor 302 may be functionalized with a hydrazide linker molecule for allowing uniform-oriented conjugation of $F_c$ region 102 of antibodies 100 to a surface of gold nano-urchins 200 thereby allowing antigen binding regions ($F_{ab}$ regions 104) of antibodies 100 free for binding with cancer biomarkers 316. Having uniformly oriented antibodies 100 allows for maximum binding of the biomarker 316 and it is often detected based on a surface plasmon resonance (SPR) signal that changes as the analyte binds to the antibodies 100. The gold nano-urchins 200 allow easy conjugation of $F_c$ region 102 of the antibodies 100 onto the spikes 202 of the gold nano-urchins 200. The cancer biomarkers 316 in the blood serum bind to the antibodies 100 at the antigen binding sites 106a, 106b, when the sample of blood serum is introduced into the flow channel 306 of the nano-biosensor 302.

In an embodiment, the system comprises of a localized surface plasmon resonance (LSPR) based detector 320, a plasmon enhanced fluorescence (PEF) based detector 340 and a surface-enhanced Raman scattering (SERS) based detector 360, wherein each of the detectors are configured to detect cancer biomarkers 316 in the sample of blood serum. The system 300 further comprises of a chamber 318 for receiving the nano-biosensor 302. The chamber 318 may be a dark space configured to allow optical detection by the detectors provided, wherein presence of cancer biomarkers 316 in the blood serum is detected based on the analysis of blood serum by the localized surface plasmon resonance (LSPR) based detector 320, the plasmon enhanced fluorescence (PEF) based detector 340 and the surface-enhanced Raman scattering (SERS) based detector 360. Each of the detectors will now be discussed in greater detail.

Figure 3C:
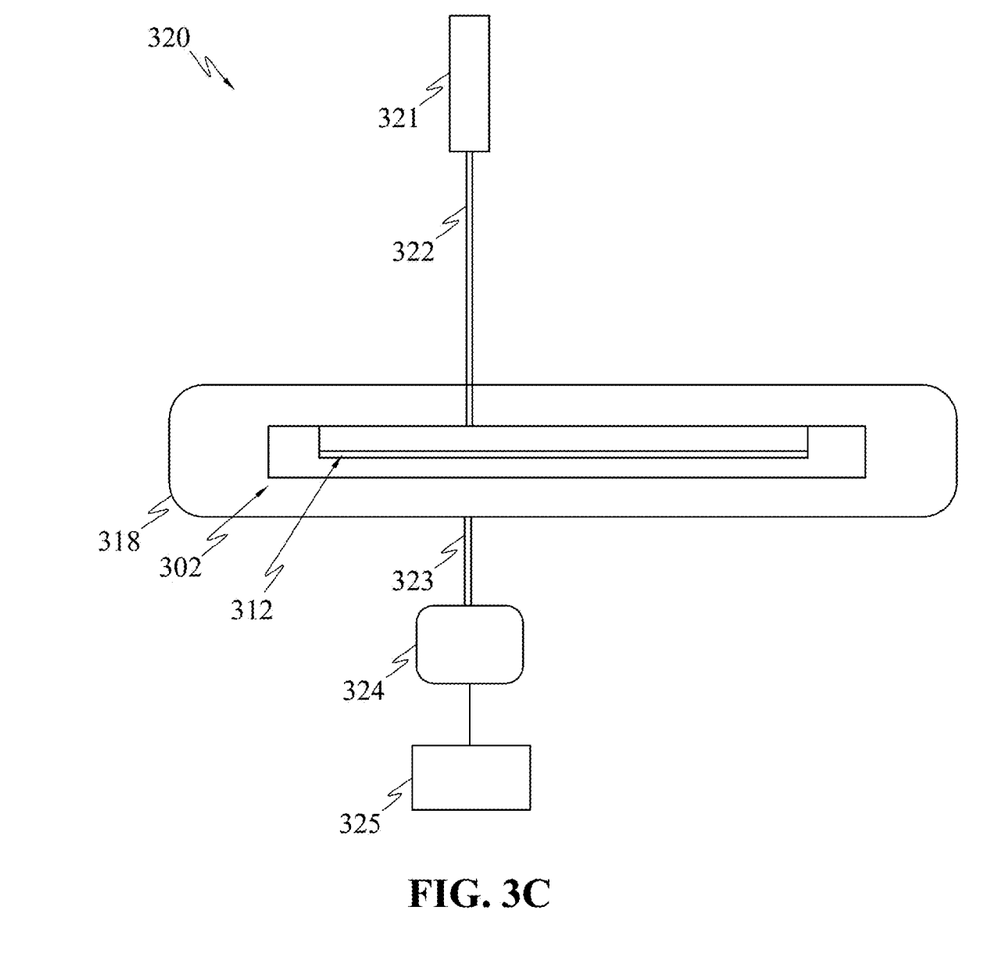
FIG. 3C is a schematic representation of a localized surface plasmon resonance (LSPR) based detector 320 of a multimodal detection system 300, in accordance with an embodiment.

Referring to FIGS. 3A and 3C, the multimodal detection system 300 with localized surface plasmon resonance (LSPR) based detector 320 is disclosed, in accordance with an embodiment. The LSPR based detector 320 comprises of a first optical source 321, a first optical fibre 322, a second optical fibre 323, a first spectrometer 324 and a first processing module 325. The first optical source 321 and the first optical fibre 322 may be provided on an upper side of the chamber 318 that receives the nano-biosensor 302. The first optical source 321 may be configured to generate halogen light. The first optical fibre 322 may be connected to the first optical source 321 and may be configured to direct the halogen light generated by the first optical source 321 onto the nano-biosensor 302 to generate surface plasmon (not shown in figures) at the active site 312 of the nano-biosensor 302. A part of the halogen light may pass-through the active site 312 of the nano-biosensor 302. The second optical fibre 323, first spectrometer 324 and the first processing module 325 may be disposed on another side of the chamber 318, opposite to that of the first optical source 321 and the first optical fibre 322. The second optical fibre 323 may be connected to the first spectrometer 324, and the first processing module 325 may be connected to the first spectrometer 324. The second optical fibre 323 may be configured to direct the halogen light exiting from the active site 312 of the nano-biosensor 302 to the first spectrometer 324. The first spectrometer 324 may be configured to measure wavelength of the halogen light exiting from the nano-biosensor 302, wherein the measuring may be done once before the blood serum is introduced in the nano-biosensor 302 and once after the blood serum is introduced in the nano-biosensor 302. The first processing module 325 connected to the first spectrometer 324 may be configured to carry out spectral analysis of the halogen light exiting from the nano-biosensor 302.

In an embodiment, the first processing module 325 of the LSPR based detector 320 may be configured to obtain a visible range absorbance spectrum of the halogen light exiting from the nano-biosensor 302 once before the blood serum is introduced in the nano-biosensor 302 and once after the blood serum is introduced in the nano-biosensor 302. Upon obtaining both visible range absorbance spectra from the active site 312 of the nano-biosensor 302, the first processing module 325 may be configured to compare the visible range absorbance spectra of the halogen light exiting from the nano-biosensor 302. The first processing module 325 may be configured to indicate binding of cancer biomarkers 316 to the antibodies 100 based on comparison of the visible range absorbance spectra obtained before and after introduction of the blood serum into the nano-biosensor 302.

In an embodiment, the first processing module 325 may be, but not limited to, a computer with plurality of input and output peripherals provided that may be configured to carry out spectral analysis of a spectrum of light.

Figure 3D:
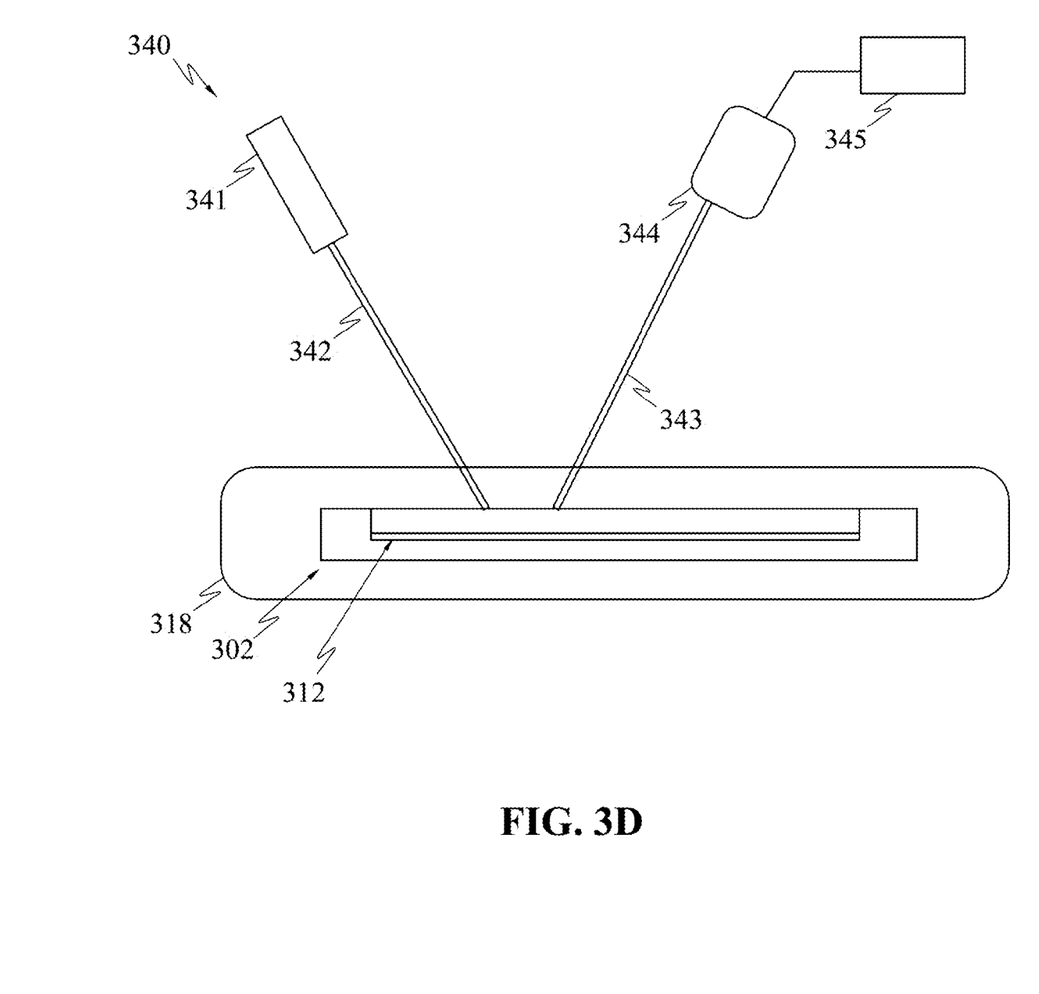
FIG. 3D is a schematic representation of plasmon enhanced fluorescence (PEF) based detector 340 of a multimodal detection system 300, in accordance with an embodiment.

Referring to FIGS. 3A and 3D, multimodal detection system 300 with plasmon enhanced fluorescence (PEF) based detector 340 is disclosed, in accordance with an embodiment. The PEF based detector 340 comprises a second optical source 341, a third optical fibre 342, a fourth optical fibre 343, a second spectrometer 344 and a second processing module 345. All of the second optical source 341, the third optical fibre 342, the fourth optical fibre 343, the second spectrometer 344 and the second processing module 345 are provided on the upper side of the chamber 318, wherein the second optical source 341 may be provided at an angle. The second optical source 341 may be configured to generate ultraviolet light (UV laser). The third optical fibre 342 may be connected to the second optical source 341 and may be configured to direct the UV laser generated by the second optical source 341 onto the nano-biosensor 302 for exciting the antibodies 100 and cancer biomarkers 316 introduced into the nano-biosensor 302 thereby resulting in fluorescence emission. The fluorescence emission will be enhanced due high-intensity electromagnetic field at the spikes of the gold nano-urchins 200 coupling with the intrinsic fluorophores of $F_c$ region 102 of the antibodies 100 and the cancer biomarkers 316 in the sample of blood serum. A part of the enhanced fluorescence may reflect from the active site 312 of the nano-biosensor 302. The fourth optical fibre 343 may be connected to the second spectrometer 344, and the second processing module 345 may be connected to the second spectrometer 344. The fourth optical fibre 343 may be configured to direct the enhanced fluorescence from the active site 312 of the nano-biosensor 302 to the second spectrometer 344. The second spectrometer 344 may be configured to measure wavelength of the enhanced fluorescence, wherein the measuring may be done once before the blood serum is introduced in the nano-biosensor 302 and once after the blood serum is introduced in the nano-biosensor 302 The second processing module 345 connected to the second spectrometer 344 may be configured to analyse the fluorescence emission reflected from the nano-biosensor 302.

In an embodiment, the second processing module 345 of the PEF based detector 340 may be configured to obtain fluorescence emission from the nano-biosensor 302 once before the blood serum is introduced in the nano-biosensor 302 and once after the blood serum is introduced in the nano-biosensor 302. Upon obtaining both the fluorescence emissions from the active site 312 of the nano-biosensor 302, the second processing module 345 may be configured to compare the obtained fluorescence emission. The second processing module 345 may be configured to indicate binding of cancer biomarkers 316 to the antibodies 100 based on comparison of the fluorescence emission obtained before and after introduction of the blood serum into the nano-biosensor 302.

In an embodiment, the second processing module 345 may be, but not limited to, a computer with plurality of input and output peripherals provided that may be configured to analyse the fluorescence emission.

Figure 3E:
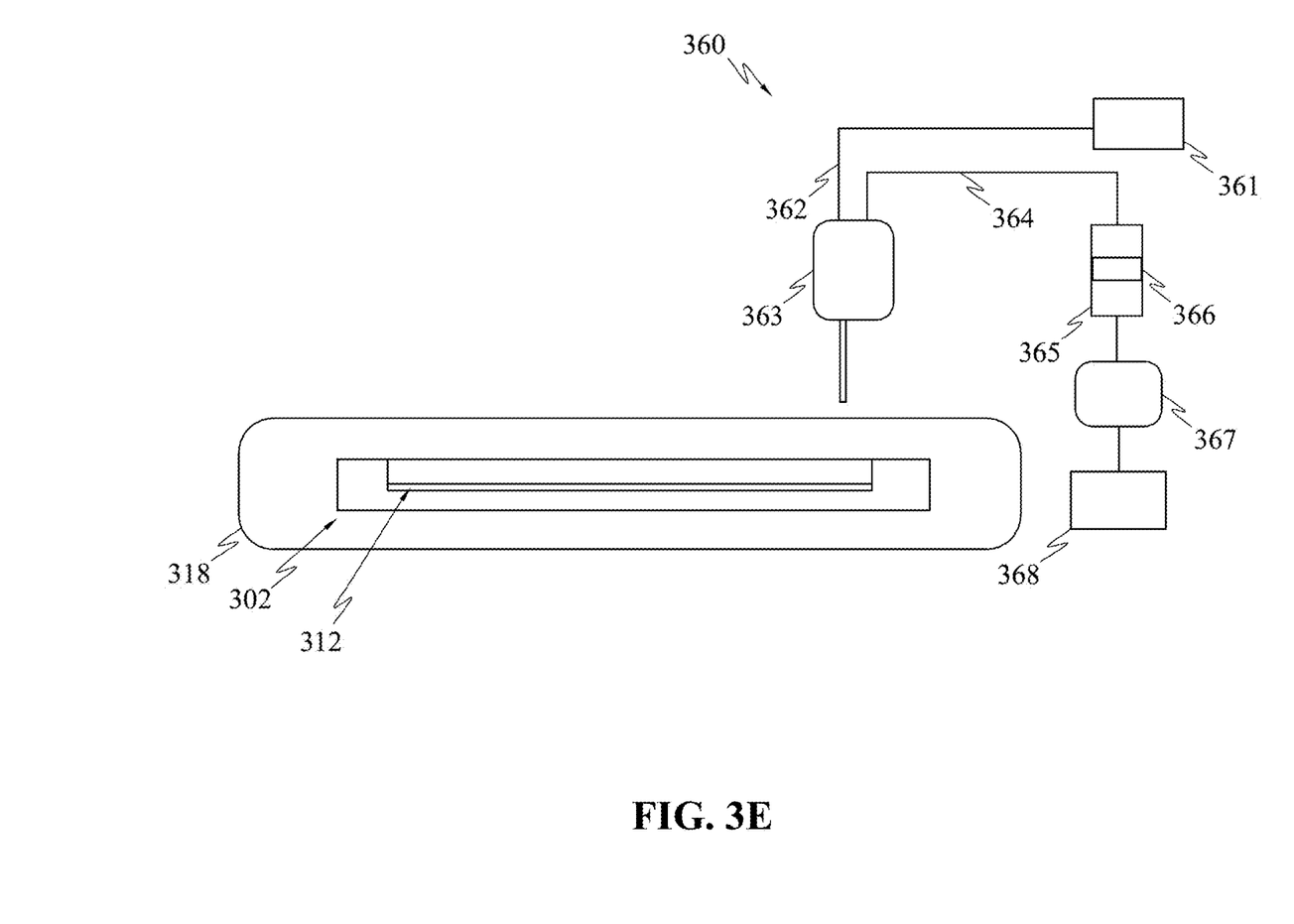
FIG. 3E is a schematic representation of a surface-enhanced Raman scattering (SERS) based detector 360 of a multimodal detection system 300, in accordance with an embodiment.

Referring to FIGS. 3A and 3E, multimodal detection system 300 with surface-enhanced Raman scattering (SERS) based detector 360 is disclosed, in accordance with an embodiment. The SERS based detector 360 comprises a third optical source 361, a fifth optical fibre 362, a Raman probe 363, a sixth optical fibre 364, an inline filter holder 365 with a notch filter 366, a Raman spectrometer 367 and a third processing module 368. All of the third optical source 361, the third optical source 361, the fifth optical fibre 362, the Raman probe 363, the sixth optical fibre 364, the inline filter holder 365, the Raman spectrometer 367 and the third processing module 368 may be provided on the upper side of the chamber 318. The third optical source 361 may be configured to generate a laser light. The fifth optical fibre 362 may be connected to the third optical source 361 on one side and the Raman probe 363 on another side, wherein the fifth optical fibre 362 may be configured to direct the laser light from the third optical source 361 to the Raman probe 363. The Raman probe 363 may be configured to focus the laser light onto the active site 312 of the nano-biosensor 302 thereby resulting in enhanced Raman scattering at the active site 312 of the nano-biosensor 302. The Raman probe 363 may also be configured to receive the enhanced scattered Raman signals from the active site 312 of the nano-biosensor 302.

In an embodiment, the sixth optical fibre 364 may be connected to the Raman probe 363 on one side and the inline filter holder 365 on another side. The sixth optical fibre 364 may be configured to direct the scattered Raman signals from the Raman probe 363 to the inline filter holder 365. The inline filter holder 365 may be provided with a notch filter 366. The inline filter holder 365 comprising the notch filter 366 may be disposed between the Raman probe 363 and the Raman spectrometer 367. The notch filter 366 may be configured to filter out incident laser wavelength and thereby allow only the scattered Raman signals from the active site 312 of the nano-biosensor 302 to pass through. The Raman spectrometer 367 may be connected to the inline filter holder 365, and the third processing module 368 may be connected to the Raman spectrometer 367. The filtered Raman signals from the inline filter holder 365 are then directed to the Raman spectrometer 367 for detecting the Raman signals. The Raman spectrometer 367 may be configured to detect Raman signals. The third processing module 368 connected to the third spectrometer may be configured to analyse the filtered Raman signals.

In an embodiment, the third processing module 368 of the SERS based detector 360 may be configured to obtain Raman spectrum from the nano-biosensor 302 once before the blood serum is introduced in the nano-biosensor 302 and once after the blood serum is introduced in the nano-biosensor 302. Upon obtaining both the Raman spectra from the active site 312 of the nano-biosensor 302, the third processing module 368 may be configured to compare the obtained Raman spectra. The third processing module 368 may be configured to indicate binding of cancer biomarkers 316 to the antibodies 100 based on comparison of the Raman spectra obtained before and after introduction of the blood serum into the nano-biosensor 302.

In an embodiment, the third processing module 368 may be, but not limited to, a computer with plurality of input and output peripherals provided that may be configured to analyse the Raman spectra obtained before and after introduction of the blood serum into the nano-biosensor 302.

The cancer biomarkers 316 in the blood serum play a pivotal role in cancer detection and during the treatment process, wherein continuous monitoring of the cancer biomarker 316 levels indicate effectiveness of the treatment. The multimodal optical nano-biosensor detection system 300 disclosed in the foregoing is provided for an accurate detection and analysis of cancer biomarker 316 levels in the blood serum. The technique is based on principles of combined LSPR, PEF and SERS using uniformly oriented antibodies conjugated to gold nano-urchins which can be used to obtain information about the presence or absence of cancer biomarkers in blood serum.

It shall be noted that the processes described above are described as sequence of steps; this was done solely for the sake of illustration. Accordingly, it is contemplated that some steps may be added, some steps may be omitted, the order of the steps may be re-arranged, or some steps may be performed simultaneously.

Although embodiments have been described with reference to specific example embodiments, it will be evident that various modifications and changes may be made to these embodiments without departing from the broader scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the invention but as merely providing illustrations of some of the personally preferred embodiments of this invention. Thus, the scope of the invention should be determined by the appended claims and their legal equivalents rather than by the examples given.

What is claimed is:

1. A multimodal detection system for detecting cancer biomarkers in blood serum, the system comprising:
   a nano-biosensor, comprising:
   a glass substrate with an active site for receiving a sample of blood serum, wherein the glass substrate is dimensioned to define a flow channel for introducing the sample of blood serum into the nano-biosensor;
   a layer of amino-silane compound coating over the glass substrate; and
   a plurality of gold nano-urchins bound to the layer of silicone compound, wherein the plurality of gold-nano-urchins are functionalized with a hydrazide linker molecule for allowing uniform-oriented conjugation of a $F_c$ region of antibodies to a surface of gold nano-urchins thereby allowing $F_{ab}$ regions of antibodies for binding with cancer biomarkers;
   a chamber configured to receive the nano-biosensor;
   a localized surface plasmon resonance (LSPR) based detector;
   a plasmon enhanced fluorescence (PEF) based detector; and
   a surface-enhanced Raman scattering (SERS) based detector;
   wherein the presence of cancer biomarkers in the blood serum is detected based on the analysis of blood serum by the localized surface plasmon resonance (LSPR) based detector, the plasmon enhanced fluorescence (PEF) based detector and the surface-enhanced Raman scattering (SERS) based detector.

2. The apparatus as claimed in claim 1, wherein the amino-silane compound comprises (3-Aminopropyl)triethoxysilane (APTES).

3. The apparatus as claimed in claim 2, wherein the localized surface plasmon resonance (LSPR) based detector comprising:
   a first optical source for generating halogen light;
   a first optical fibre for directing halogen light from the first optical source to pass-through the nano-biosensor to generate a surface plasmon at the nano-biosensor;
   a first spectrometer for receiving the halogen light exiting from the nano-biosensor;
   a second optical fibre for directing the received halogen light exiting from the nano-biosensor to the first spectrometer; and
   a first processing module for spectral analyses of the halogen light exiting from the nano-biosensor, wherein the first processing module is connected to the first spectrometer.

4. The apparatus as claimed in claim 3, wherein the first processing module of the LSPR based detector is configured to:
   obtain a visible range absorbance spectrum of the halogen light exiting from the nano-biosensor before introduction of the blood serum;
   obtain a visible range absorbance spectrum of the halogen light exiting from the nano-biosensor after introduction of the blood serum;
   compare the obtained visible range absorbance spectra of the halogen light exiting from the nano-biosensor before and after introduction of the blood serum; and
   indicate binding of cancer biomarkers to the antibodies based on comparison of the visible range absorbance spectra obtained before and after introduction of the blood serum into the nano-biosensor.

5. The apparatus as claimed in claim 2, wherein the plasmon enhanced fluorescence (PEF) based detector comprising:
   a second optical source for generating UV laser;
   a third optical fibre for directing the UV laser from the second optical source to the nano-biosensor for exciting the antibodies and cancer biomarkers in the nano-biosensor thereby resulting in fluorescence emission;
   a second spectrometer for receiving the fluorescence emitted from the nano-biosensor;
   a fourth optical fibre for directing the fluorescence from the nano-biosensor to the second spectrometer; and a second processing module for analysing the fluorescence emission, wherein the second processing module is connected with the second spectrometer.

6. The apparatus as claimed in claim 5, wherein the second processing module of the PEF based detector is configured to:
   obtain a fluorescence emission from the nano-biosensor before introduction of the blood serum;
   obtain a fluorescence emission from the nano-biosensor after introduction of the blood serum;
   compare the obtained fluorescence emission from the nano-biosensor before and after introduction of the blood serum; and
   indicate binding of cancer biomarkers to the antibodies based on comparison of the fluorescence emission obtained before and after introduction of the blood serum into the nano-biosensor.

7. The apparatus as claimed in claim 2, wherein the surface-enhanced Raman scattering (SERS) based detector comprising:
   a third optical source for generating laser light;
   a fifth optical fibre for directing the laser light from the third optical source to the Raman probe;
   a Raman probe for focusing the laser light onto the nano-biosensor and receiving scattered Raman signals from the nano-biosensor;
   a Raman spectrometer for detecting Raman signals;
   a sixth optical fibre for directing the laser light from the Raman probe to the Raman spectrometer;
   an inline filter holder with a notch filter provided between the Raman probe and the Raman spectrometer, wherein the notch filter is configured to filter out any incident laser wavelength thereby allowing only Raman signal; and
   a third processing module for spectral analyses of the filtered Raman signals, wherein the third processing module is connected to the Raman spectrometer.

8. The apparatus as claimed in claim 7, wherein the third processing module of the SERS based detector is configured to:
   obtain a Raman spectrum from the nano-biosensor before introduction of the blood serum;
   obtain a Raman spectrum from the nano-biosensor after introduction of the blood serum;
   compare the obtained Raman spectra from the nano-biosensor before and after introduction of the blood serum; and
   indicate binding of cancer biomarkers to the antibodies based on comparison of the Raman spectra obtained before and after introduction of the blood serum into the nano-biosensor.

* * * * *